United States Patent
Gerlach et al.

(10) Patent No.: US 6,350,285 B2
(45) Date of Patent: *Feb. 26, 2002

(54) IMPLANT HOLDER

(75) Inventors: Roland Gerlach, Guxhagen; Josef Hannappel, Pulheim; Juergen Reuter, Alheim; Dorothea Rohrmann, Langerwehe, all of (DE)

(73) Assignee: CareMed Medical Produkte AG, Dresden (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/350,285

(22) Filed: Jul. 9, 1999

(30) Foreign Application Priority Data

Jul. 15, 1998 (DE) .......................... 198 31 699

(51) Int. Cl.$^7$ ................ A61F 2/00; A61F 2/04
(52) U.S. Cl. ................ 623/23.76; 623/23.64; 600/37; 606/151
(58) Field of Search .............. 623/23.64, 11.11, 623/23.5, 23.74, 23.76, 23.72; 600/37; 606/151

(56) References Cited

U.S. PATENT DOCUMENTS

| | | | | |
|---|---|---|---|---|
| 3,489,647 A | * | 1/1970 | Kolobow ................ 623/23.65 |
| 3,988,411 A | * | 10/1976 | Capozza ................ 264/184 |
| 4,497,074 A | | 2/1985 | Rey et al. ................ 623/1.24 |
| 4,627,429 A | * | 12/1986 | Tsuk ................ 604/307 |
| 4,963,154 A | * | 10/1990 | Anapliotis et al. ........ 623/22 |
| 4,969,902 A | * | 11/1990 | Ravo ................ 623/23.68 |
| 5,314,471 A | * | 5/1994 | Brauker et al. ........ 623/23.72 |
| 5,356,429 A | * | 10/1994 | Seare ................ 623/8 |
| 5,475,052 A | * | 12/1995 | Rhee et al. ............ 525/54.1 |
| 5,509,890 A | * | 4/1996 | Kazama ................ 600/37 |
| 5,824,050 A | * | 10/1998 | Karwoski et al. ........ 623/1.4 |
| 5,932,460 A | * | 8/1999 | Mills et al. ........ 604/890.1 X |
| 6,031,148 A | * | 2/2000 | Hayes et al. ............ 623/11.11 |
| 6,045,497 A | * | 4/2000 | Schweich, Jr. et al. ..... 600/37 |
| 6,120,539 A | * | 9/2000 | Eldridge et al. ........ 623/11.11 |

* cited by examiner

*Primary Examiner*—Bruce Snow
*Assistant Examiner*—Brian E. Pellegrino
(74) *Attorney, Agent, or Firm*—Diller, Ramik & Wight

(57) ABSTRACT

The implant holder comprises a screen (21) comprising on one side a tissue-compatible fibre material (25) to which the body cells grow and on the other side a smooth contact surface (23) for the implant (10). A holding fixture (26) retains the implant (10) to the screen (21). The implant holder prevents the body tissue from directly growing to the implant, which would make exchange of the implant (10) more difficult. To exchange the implant the skin (16) of the patient is cut open and the holding fixture (26) is opened. The implant holder remains in the body while the implant (10) is exchanged.

2 Claims, 1 Drawing Sheet

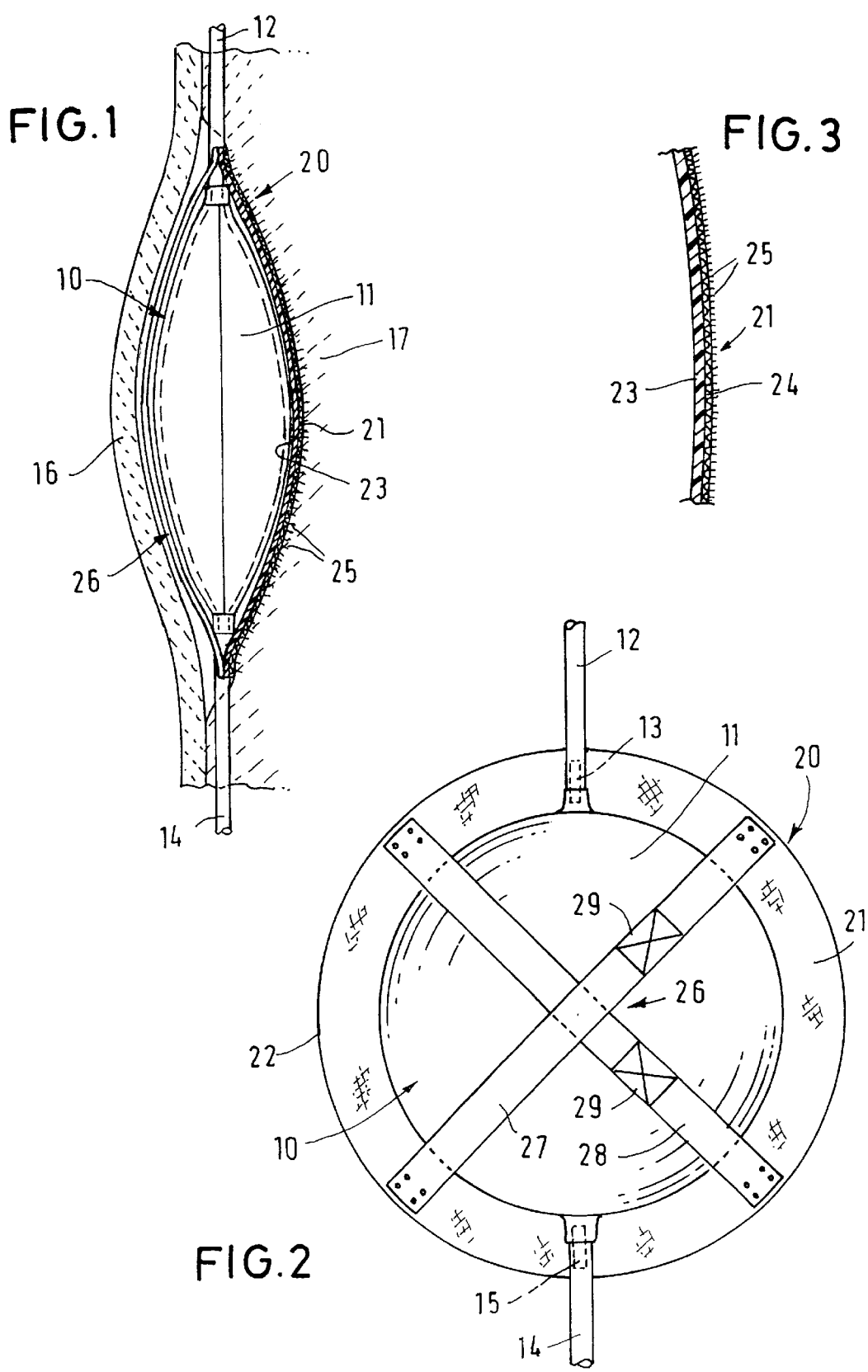

IMPLANT HOLDER

BACKGROUND OF THE INVENTION

The present invention relates to an implant holder for body implants, such as an artificial bladder, insulin pumps, a pacemaker or a drug capsule.

Implants to be implanted into the bodies of human beings or animals frequently require an access to be provided for the implants to be exchanged, the contents to be replaced or the implants to be serviced. Normally such implants possess a housing made of material tolerated by the body, to which the body cells grow in the course of time. Thus the body tissue is attached to the implant capsule. If this implant capsule is to be taken out, the body tissue must be removed first. Further, some implants require a holder which ensures that they are retained in place in the body. Such a holder for a prosthetic bladder is described in U.S. Pat. No. 4,497,074. The holder comprises bandages which are fixed to the peritoneum or the musculature and retain the prosthetic bladder.

SUMMARY OF THE INVENTION

The object of the present invention is to create an implant holder which allows implants to be exchanged, if necessary, in an easy manner without any essential stress to the body.

The implant holder according to the present invention comprises a screen to which the body tissue grows from one side whereas the other side comprises a contact surface for the implant. This contact surface is preferably smooth and tissue-rejecting. In this way a kind of pocket or nest is formed subcutaneous in the body, which accommodates the implant without the tissue completely growing around the implant. The screen further comprises a holding fixture suitable to retain the implant to the contact surface. Since implants are generally positioned immediately beneath the skin, the implant is accessible and removable through a simple skin incision without the implant adhering to the body or being retained in the body. The implant is accessible with the patient being locally anaesthetised. Thus a general anaesthesia is not required as is normally the case when the implant must be separated from the body tissue.

The screen comprises a contact surface on the side facing the implant and a layer of tissue-compatible fibre material, preferably a velours material, on the outer surface. A suitable material for the smooth contact surface is a smooth silicone foil. Silicones are tissue-compatible and the smooth foil impedes growing of the tissue to the foil.

BRIEF DESCRIPTION OF THE DRAWINGS

Hereunder an embodiment of the present invention is explained in detail with reference to the drawings in which FIG. 1 shows a side view of an artificial bladder implanted into the body, FIG. 2 shows a front view of the artificial bladder placed into the implant holder, and FIG. 3 shows a cross-sectional view of the material of the screen of the implant holder.

DESCRIPTION OF THE PREFERRED EMBODIMENT

FIG. 1 shows an implant 10 which is an artificial bladder. The implant 10 comprises a container 11 made of elastic plastic material. This container which is round as seen from the front (FIG. 2) can be axially compressed. When the axial pressure force is no longer exerted, the original form of the container is restored, i. e. the container is expanded.

A catheter 12 coming from a kidney runs into the container 11 with the catheter comprising a check valve 13. At the bottom part of the container 11 a urethral catheter 14 containing a check valve 15 leaves the container 11. The container 11 is implanted between the skin 16 and the muscular tissue 17 of the patient. The patient can compress the container 11 by exerting pressure from outside in order to press fluid contained therein into the urethral catheter 14. Then the container 11 tends to expand again thus producing a suction effect so that urine is drawn off the kidney.

The implant 10 is exchangeably placed into the implant holder 20. The implant holder 20 comprises a screen 21 which separates the implant 10 from the muscular tissue 17. The screen 21 is large enough to completely cover the horizontal projection of the implant 10 and even rises above it as can be seen in FIG. 2 so that the screen with a projecting edge 22 juts out the contour of the implant 10.

The screen 21 comprises a foil layer 23 of smooth silicone foil on its inner surface facing the implant 10. This foil layer is 1–1.5 mm thick. On the outer surface of the foil layer 23 there is a velours layer 24 made of tissue-compatible fibre material, preferably Dakron velours. The fine hair of this velours layer 24 stands out to the outside and forms the fibre material 25 to which grows the muscular tissue 17.

To the edge 22 of the screen 21 a holding fixture 26 is attached which retains the implant 10 to the inner surface of the screen 21. This holding fixture 26 here comprises two bandages 27, 28 arranged crosswise both provided with a lock 29.

The bandages 27, 28 are made up of relatively small strips of a material to which the cells cannot easily grow. For the implant 10, too, a material is selected which does not allow, to the extent possible, adhesion to the body tissue.

While one side of the implant is completely covered by the screen, the other side of the implant is exposed with a small portion (less than 10%) being merely covered by the holding fixture 26. Alternatively, it is possible to attach the holding fixture to the screen 21 so that the side of the implant not facing the screen is completely exposed.

If it is necessary to exchange the implant 10, the skin 16 is opened by one incision or several incisions. Then the locks 29 are unlocked and the implant 10 is accessible for removal. The implant holder 20 remains in the body while the implant 10 is taken out and replaced, if necessary. Following that the incision in the skin 16 is closed and sewn.

If the implant 10 is an artificial bladder connected to catheters 12, 14 as in the present embodiment, the catheter connection should be detachable in order to allow the catheters to remain in the body when the bladder is exchanged.

What is claimed is:

1. A combination comprising a body implant and an implant holder for holding said body implant, said implant holder including two layers of material, one of said layers of material being tissue-compatible to which body cells grow, another of said layers of material having an implant contacting tissue-rejecting surface and another surface opposite thereto, said another surface being in opposing relationship to said one layer and being secured thereto, said body implant being located exteriorly of and against said implant contacting tissue-rejecting surface, said body implant including an outer surface which substantially precludes tissue from adhering thereto, means for holding said body implant against said implant contacting tissue-rejecting surface, and said holding means includes a strip of material which substantially precludes tissue from adhering thereto.

2. The combination as defined in claim 1 wherein said one and another layers are each substantially flat.

* * * * *